US008461146B2

United States Patent
Seol et al.

(10) Patent No.: US 8,461,146 B2
(45) Date of Patent: Jun. 11, 2013

(54) PHARMACEUTICAL COMPOSITION FOR THE TREATMENT OF PREMATURE EJACULATION

(75) Inventors: Hyun Uk Seol, Seoul (KR); Young Sung Lee, Seoul (KR); Young Hun Kim, Suwon-si (KR); Kyeong Bae Kim, Seoul (KR); Jeong Min Seo, Seoul (KR); Kyoung Kyu Ahn, Suwon-si (KR)

(73) Assignees: Yuhan Corporation, Seoul (KR); Hyun Uk SEOL, Seoul (KR)

( * ) Notice: Subject to any disclaimer, the term of this patent is extended or adjusted under 35 U.S.C. 154(b) by 278 days.

(21) Appl. No.: 12/993,418

(22) PCT Filed: May 19, 2009

(86) PCT No.: PCT/KR2009/002636
§ 371 (c)(1),
(2), (4) Date: Nov. 18, 2010

(87) PCT Pub. No.: WO2009/142428
PCT Pub. Date: Nov. 26, 2009

(65) Prior Publication Data
US 2011/0071138 A1    Mar. 24, 2011

(30) Foreign Application Priority Data
May 19, 2008 (KR) .................. 10-2008-0046199

(51) Int. Cl.
*A61K 31/55* (2006.01)
*A61K 31/137* (2006.01)
*A61K 31/138* (2006.01)
*A61P 15/00* (2006.01)

(52) U.S. Cl.
USPC ........... 514/217; 514/649; 514/651; 514/650; 564/306; 564/338; 564/348

(58) Field of Classification Search
None
See application file for complete search history.

(56) References Cited

U.S. PATENT DOCUMENTS
6,946,141 B2 *  9/2005  Tam et al. .................. 424/423

FOREIGN PATENT DOCUMENTS
WO    2008/037045 A2    4/2008

OTHER PUBLICATIONS

Giuliano et al., "The Pharmacological Treatment of Premature Ejaculation," BJU International, 2008, vol. 102, No. 6, pp. 668-675.
European Patent Office, European Search Report issued in corresponding EP Application No. 09750750.3, dated Jun. 29, 2012.
Kim et al., "Efficacy and Safety of Fluoxetine, Sertraline and Clomipramine in Patients with Premature Ejaculation: A Double-Blind, Placebo Controlled Study," The Journal of Urology, 1998, vol. 159, pp. 425-427.
Marcel D. Waldinger, "Premature Ejaculation: Definition and Drug Treatment," Drugs, 2007, vol. 64, No. 4, pp. 547-568.
McMahon et al., "Pharmacological Treatment of Premature Ejaculation," Current Opinion in Urology, 1999, vol. 9, No. 6, pp. 553-561.
Evanoff et al., "Treatment of Premature Ejaculation," The Journal of Family Practice, 1998, vol. 46, No. 4, pp. 280-281.

* cited by examiner

Primary Examiner — Sreeni Padmanabhan
Assistant Examiner — Irina Neagu
(74) Attorney, Agent, or Firm — Sughrue Mion, PLLC (57) ABSTRACT

The present invention provides an oral pharmaceutical composition for the treatment of premature ejaculation, and the composition provides the effective and excellent treatment of premature ejaculation as well as reduced side effects like nausea, vomiting, drowsiness, sedation effect, awakening effect, and weight-loss etc.

12 Claims, 2 Drawing Sheets

PHARMACEUTICAL COMPOSITION FOR THE TREATMENT OF PREMATURE EJACULATION

FIELD OF THE INVENTION

The present invention relates to a pharmaceutical composition for the treatment of premature ejaculation, comprising clomipramine or pharmaceutically acceptable salts, sertraline or pharmaceutically acceptable salts and fluoxetine or pharmaceutically acceptable salts as active ingredients.

BACKGROUND OF THE INVENTION

Premature ejaculation (PE), also known as rapid ejaculation, is defined as occurring if the man persistently or recurrently ejaculates in response to minimal stimulation before, during, or shortly after penetration and before the patient (or partner) wishes it. Premature ejaculation is mainly caused by psychological factors. It has hereditary characteristics and abnormality in the neuron or other networks can also contribute to premature ejaculation. Premature ejaculation is one of quite common sexual dysfunctions and ⅓ of men suffer from premature ejaculation.

According to WHO, premature ejaculation is quantitatively defined as the intravaginal ejaculation latency time (IELT) is 60 seconds or less. It is known that ejaculation delay is related to the activation of 5HT2c, while rapid ejaculation is associated with 5HT1a. It is assumed that the low level of 5HT (serotonin) neurotransmission, the hypofunction of 5HT2c receptor, or the hyperfunction of 5HT1a leads to premature ejaculation. It can also be related to other factors including hypersensitivity of nervous system, penis sensitivity, somatic cell-vulnerability, deterrent effect of the serotonin operating system, etc. (US Publication No. 2007-0043030; *Trends in Neuroscience*, 2007, (30):79-84).

Premature ejaculation is the most common symptom of the male sexual dysfunction, but there has not been conducted insufficient research thereon. A research by Masters and Johnson in 1970 announcing that premature ejaculation could be easily fixed by behavior therapy was the established theory, and the cause of the premature ejaculation was considered as similar to that of impotence or libido degradation. However, it has been found that behavior therapy has the limits and the medical treatment of premature ejaculation came to attention in 1990s.

In the early stage of medical treatment of premature ejaculation, clomipramine (Anafranil®) which is a representative tricyclic antidepressant (TCAs) was used. There is reported the ejaculation latency effect by medicating clomipramine with the oral dose of 25 mg or 50 mg per day (*J Clin Psychiatry*. 1995, (56):402-407). Further, it is reported that when 50 mg of clomipramine was administered to premature ejaculation patients with an average age of 44, some side effects including constipation, dry-mouth, nausea, drowsiness, headache and dizziness, etc. were shown up, although ejaculation was delayed (*The Journal of Urology*, 1998, (159):425-427). Such side effects occur since clomipramine affect not only serotonin but also other neurotransmitters.

For the above problems, researchers have begun to focus on a Selective Serotonin Reuptake Inhibitor (SSRI) for the treatment of premature ejaculation. Sertraline (Zoloft®), one of representative SSRIs, was used for the treatment of premature ejaculation. It is reported that when 50 mg to 200 mg per day of sertraline was administered to premature ejaculation patients, while the ejaculation was delayed, side effects including nausea, vomiting, etc. also occurred and such side effects lead to lowering the medication effect (*The Journal of Urology*, 1998, (159):1935-1938; U.S. Pat. No. 4,940,731).

Among other SSRIs, fluoxetine (Prozac®), known as an antidepressant, was administered for the treatment of premature ejaculation. U.S. Pat. No. 5,151,448 describes that fluoxetine was administered to the patients with premature ejaculation. Also, as reported in *The Journal of Urology*, 1998, (159):425-427, 40 mg of fluoxetine was administered to premature ejaculation patients, but the ejaculation delay effect was weak. Besides, the side effects including drowsiness, dry-mouth, nausea, vomiting, etc. were reported. When fluoxetine was administered to premature ejaculation patients as shown in *The Journal of Urology*, 2003, (170):164-165, the side effects such as nausea, headache, and insomnia occurred. Therefore, fluoxetine cannot be successfully used for the treatment of premature ejaculation.

U.S. Pat. No. 6,495,154 describes a rapid-release pharmaceutical formulation containing clomipramine which can be conveniently administered on demand, but did not suggest concrete solutions to the side effects mentioned above. US Publication No. 2007-0043030 also describes a composition for pulmonary inhalation comprising clomipramine in order to accomplish rapid treatment effect and to reduce side effects. However, there was no concrete results showing the treatment effect of medicine and diminishing the side effects. Furthermore, there is not suggested any combinational compositions of various antidepressants or other therapeutic agents.

Therefore, new therapeutic agents for the treatment of premature ejaculation, which has effective and excellent treatment effects and reduce side effects like nausea, vomiting, drowsiness, sedation effect, awakening effect, and weight-loss, etc. has been required in the relevant industry.

SUMMARY OF THE INVENTION

Accordingly, it is an object of the present invention to provide a pharmaceutical composition for the treatment of premature ejaculation.

It is another object of the present invention to provide a method for treating premature ejaculation.

In accordance with one aspect of the present invention, there is provided a pharmaceutical composition for the treatment of premature ejaculation, comprising clomipramine or a pharmaceutically acceptable salt thereof, sertraline or a pharmaceutically acceptable salt thereof and fluoxetine or a pharmaceutically acceptable salt thereof as active ingredients.

In accordance with another aspect of the present invention, there is provided a method for the treatment of premature ejaculation, comprising administering a composition which comprises clomipramine or a pharmaceutically acceptable salt thereof, sertraline or a pharmaceutically acceptable salt thereof and fluoxetine or a pharmaceutically acceptable salt thereof as active ingredients, to a subject in need of treatment of premature ejaculation.

BRIEF DESCRIPTION OF DRAWINGS

The above and other objects and features of the present invention will become apparent from the following description of the invention, when taken in conjunction with the accompanying drawings, which respectively show.

DETAILED DESCRIPTION OF THE INVENTION

A pharmaceutical composition according to the present invention will now be described more fully with respect to exemplary embodiment of the invention.

The present inventors have endeavored to develop a pharmaceutical composition for the treatment of premature ejaculation, and found that the oral administration of a mixture of clomipramine, sertraline and fluoxetine treats premature ejaculation and reduces side effects significantly.

More particularly, the present inventors have found that when administered in a mixture of clomipramine, sertraline and fluoxetine, drug adsorption increases through the drug interactions.

The terms "clomipramine," "sertraline" and "fluoxetine," as used herein, mean each free base form thereof "A pharmaceutically acceptable salt" of clomipramine, sertraline or fluoxetine refers to nontoxic salts in a dose, and includes conventional salts such as inorganic acids, organic acids or nontoxic salts.

Examples of such inorganic acids include, but are not limited to, hydrochloric acid, nitric acid, phosphoric acid, sulfuric acid, hydrobromic acid, hydriodic acid, nitrous acid, and phosphorous acid. Examples of said organic acids include acetic acid, lactic acid, citric acid, malic acid, succinic acid, fumaric acid, maleic acid, tartaric acid, benzoic acid, phthalic acid, gluconic acid, saccharinic acid, methane sulfonic acid, ethane disulfonic acid, aliphatic mono and dicarboxylate, phenyl-substituted alkanoate, hydroxyl alkanoate and alkanedioate, aromatic acid, and aliphatic and aromatic sulfonic acid. Preferred organic acid is hydrochloric acid (hydrochloride).

Said nontoxic salts include, but are not limited to, sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butene-1,4-dioate, hexane-1,6-dioate, benzoate, chlorobenzoate, methylbenzoate, dinitro benzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, beta-hydroxybutyrate, glycolate, malate, tartrate, methanesulfonate, propanesulfonate, naphthalene-1-sulfonate, naphthalene-2-sulfonate, and mandelate.

The present invention provides a pharmaceutical composition for the treatment of premature ejaculation, comprising clomipramine or a pharmaceutically acceptable salt thereof, sertraline or a pharmaceutically acceptable salt thereof and fluoxetine or a pharmaceutically acceptable salt thereof as active ingredients.

In the pharmaceutical composition, clomipramine or a pharmaceutically acceptable salt thereof, sertraline or a pharmaceutically acceptable salt thereof and fluoxetine or a pharmaceutically acceptable salt thereof are preferably contained in the weight ratio of about 1:1~2:0.5~1.

According to an aspect of the present invention, a pharmaceutical composition for the treatment of premature ejaculation comprising 0.7~75.0 mg of clomipramine, 1.1~113.0 mg of sertraline and 0.5~59.0 mg of fluoxetine as an effective daily dose for a human is provided. Preferably, a pharmaceutical composition for the treatment of premature ejaculation comprising 0.7~22.5 mg of clomipramine, 1.1~33.9 mg of sertraline and 0.5~17.7 mg of fluoxetine as an effective daily dose for a human is provided. More preferably, a pharmaceutical composition for the treatment of premature ejaculation comprising 2.2~22.5 mg of clomipramine, 3.3~33.9 mg of sertraline and 1.7~17.7 mg of fluoxetine as an effective daily dose for a human is provided. Most preferably, a pharmaceutical composition for the treatment of premature ejaculation comprising 7.5 mg of clomipramine, 11.3 mg of sertraline and 5.9 mg of fluoxetine as an effective daily dose for a human is provided.

The inventive treatment drug for premature ejaculation shows less side effects and significant treatment effects through the combination of clomipramine, sertraline and fluoxetine, and in particular shows maximized treatment effects and minimized side effects in said dose range.

The amounts of clomipramine, sertraline and fluoxetine herein represent the calculated values based on the free base forms of each active ingredient.

The pharmaceutical composition of the present invention may be administered orally, e.g., in a tablet, capsule, suspension, granule, gel, pill, tincture, decoction, infusion, spirit, fluid extract, elixir, extract, syrup, powder, aromatic water, lemonade and the like.

In the pharmaceutical composition of the present invention, tablets may be, for example, in the form of sugar-coated tablets, film-coated tablets, enteric-coated tablets, peroral tablets, sublingual tablets, buccal tablets, chewable tablets, dispensing tablets, multilayered tablets, press-coated tablets, effervescent tablets, solution tablets, hypodermic tablets and the like. It should be understood that various modifications and changes may be made for said tables by those skilled in the art The pharmaceutical composition of the present invention may also be prepared in the form of sustained-release formulations, controlled-release formulations, repeat-action formulations, immediate-release formulations, fast-disintegrated formulations and like.

According to another aspect of the present invention, the pharmaceutical composition of the present invention may comprise 0.7~75.0 mg of clomipramine, 1.1~113.0 mg of sertraline and 0.5~59.0 mg of fluoxetine as active ingredients in a unit dosage form, in combination with a pharmaceutically acceptable carrier. Preferably, the composition may comprise 0.7~22.5 mg of clomipramine, 1.1~33.9 mg of sertraline and 0.5~17.7 mg of fluoxetine as active ingredients in a unit dosage form, in combination with a pharmaceutically acceptable carrier. More preferably, the composition may comprise 2.2~22.5 mg of clomipramine, 3.3~33.9 mg of sertraline and 1.7~17.7 mg of fluoxetine as active ingredients in a unit dosage form, in combination with a pharmaceutically acceptable carrier. Most preferably, the composition may comprise 7.5 mg of clomipramine, 11.3 mg of sertraline and 5.9 mg of fluoxetine as active ingredients in a unit dosage form, in combination with a pharmaceutically acceptable carrier.

The pharmaceutical composition for the treatment of premature ejaculation may comprise clomipramine or a pharmaceutically acceptable salt thereof, sertraline or a pharmaceutically acceptable salt thereof and fluoxetine or a pharmaceutically acceptable salt thereof together with a pharmaceutically acceptable carrier.

The pharmaceutically acceptable carriers may include additives such as e.g., excipients, disintegrants, binders, lubricants, emulsifiers, suspending agents, stabilizers and the like. If desired, sweetening and/or flavoring agents may be added as well. The pharmaceutical composition of the present invention may be administered orally in various formulations, such as a tablet, capsule, aqueous liquid or suspension and the like. For tablets, carriers such as lactose and corn starch, etc. and lubricants such as magnesium stearate, etc. may be conventionally added. For capsules, lactose and/or dried corn starch may be used as diluents. For aqueous liquids, the active ingredients may be formulated in combination with emulsifiers and/or suspending agents. If desired, a specific sweetening and/or flavoring agents may be added.

The pharmaceutical composition of the present invention may be in the form of pharmaceutical formulations, e.g., in the form of solid, semi-solid or liquid forms. The formulations may contain a mixture of organic or inorganic carriers or excipients suitable for external, internal or parenteral use.

The pharmaceutical composition of the present invention may contain one or more pharmaceutically acceptable carriers in the form of a tablet, pellet, capsule, liquid, emulsifier, suspending agent, troche and other suitable forms, binders (e.g., microcrystalline cellulose, gum tragacanth or gelatin), excipients (e.g., starch or lactose), disintegrants (e.g., alginic acid, primogel or corn starch), lubricants (e.g., magnesium stearate or sterotex), glidants (e.g., colloid silicon dioxide), sweeteners (e.g., sucrose or saccharin), or flavoring agents (e.g., peppermint, methyl salicylate or orange flavor) may be added. Capsules in a unit dosage form may contain liquid carriers (e.g., polyethylene glycol or fatty acid oil) in addition to said additives. Other various substances, such as coatings, may be used to convert physical forms of a dosage unit. For example, a tablet or pill may be coated with sugars, shellacs or other coating agents. Syrup may contain sucrose as a sweetening agent, specific preservatives, dyes, coloring and/or flavoring agents. The additives used in preparing such various preparations should be pharmaceutically pure and nontoxic.

The inventive composition also may be in the form of solution or suspension, and may contain one or more adjuvants selected from the group consisting of sterilized diluents (e.g., water for injection), saline solutions (e.g., sodium chloride or mannitol), fixed oils, polyethylene glycol, glycerin, propylene glycol or other synthetic solvents, antibacterial agents (e.g., benzyl alcohol or methylparaben), antioxidants (e.g., ascorbic acid or sodium bisulfide), chelating agents (e.g., EDTA or ethylene diaminetetraacetic acid) and buffers (e.g., acetic acid salt, citric acid salt or phosphoric acid salt). Parenteral formulations may be packaged into amples, disposable syringes, or multiple dose vials made of glass or plastic.

The pharmaceutical composition of the present invention for the treatment of premature ejaculation can further contain, in addition to clomipramine, sertraline and fluoxetine, other drugs, e.g., one or more selected from the group consisting of serotonin agonists, serotonin antagonists, adrenergic agonists, adrenergic antagonists, adrenergic neuron blockers, impotence treatment drugs, phosphodiesterase 5 inhibitors, erection inducers and a combination thereof. In particular, phosphodiesterase 5 inhibitors include, but are not limited to, silenafil, tadalafil, vardenafil, udenafil and the like, and erection inducers include, but are not limited to, phentolamine, papaverine, alprostadil, etc. It should be understood that, if desired, those skilled in the art can select suitable drugs among said drugs, and can use another additional drugs together with said drugs.

The pharmaceutical composition of the present invention may be administered to a patient prior to engaging in sexual activity, preferably 30 min to 3 hours prior to engaging in sexual activity. The administration method may be changed depending on the characteristics of a patient.

As mentioned above, the pharmaceutical composition of the present invention, comprising clomipramine, sertraline and fluoxetine as active ingredients, provides the effective and excellent treatment of premature ejaculation as well as reduced side effects like nausea, vomiting, drowsiness, sedation effect, awakening effect, and weight-loss, etc.

Furthermore, the composition is efficacious in enhancing dosage effects and patients' compliances, by minimizing side effects resulted from each drug.

Whereas, the present invention also provides a method for the treatment of premature ejaculation comprising administering a composition which comprises clomipramine or pharmaceutically acceptable salts thereof, sertraline or pharmaceutically acceptable salts thereof and fluoxetine or pharmaceutically acceptable salts thereof as active ingredients, to a subject in need of treatment of premature ejaculation. The subject is preferably a mammal, more preferably a human.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

Example 1

Pharmacokinetics Study

<1-1> Materials and Methods 7-week-old male Crl:CD (SD) rats weighing around 200 g were fasted for 16 hours, and then cannulated with polyethylene tubing (PE-50) in the carotid artery and divided into 4 groups of 10 rats. The rats of Group 1 were orally administered with a single dose of clomipramine 2.70 mg/kg; Group 2, with sertraline 6.02 mg/kg; Group 3, with fluoxetine 2.41 mg/kg; and Group 4, with a triple-drug combination (a dose of clomipramine 2.70 mg/kg, sertraline 6.02 mg/kg and fluoxetine 2.41 mg/kg). Blood samples (about 200 µl) were collected by polyethylene tubing at 0.5, 1, 2, 3, 4, 5, 7, 9, 11 and 24 hours after the drug administration. Rats were supplemented with about 200 µl of heparinized saline (20 IU/ml) at each sampling times. The collected blood samples were centrifuged (MicroMax, International Equipment Company, USA) at 10,000 rpm for 1 min to obtain plasma samples, and then the amounts of clomipramine, sertraline and fluoxetine in the plasma samples were determined by using simultaneous LC/MS/MS method.

<1-2> Evaluation Methods

The maximum plasma concentration (Cmax) and the time to reach Cmax (Tmax) were obtained from the plasma concentration-time curve. The area under the plasma concentration-time curve (AUC) was calculated by using the trapezoidal rule.

<1-3> Results

The administration of triple-drug combination of the present invention led to the increases in Cmax and AUC of fluoxetine (known as a substrate of CYP2C9, 2C19 and 2D6 (a major enzyme)) in all animals, owing to the inhibition of CYP2D6 and CYP2C9 by clomipramine and sertraline. In case of clomipramine, the increases of Cmax and AUC were detected due to the inhibition of CYP2D6 by fluoxetine and sertraline. In case of sertraline (known as a substrate metabolized by various enzymes such as CYP2C9, 2C19, 2D6 and 3A4), Cmax and AUC were higher than those from the single drug administration data, but only AUC increased significantly.

According to the present invention, single-oral administration of the triple-drug combination resulted in escalated systemic exposure of clomipramine, fluoxetine and sertraline in the body than single drug administration, and drug-drug interaction was clearly shown in order of fluoxetine>clomipramine>sertraline.

Results of the determination of AUC and $C_{max}$ with triple-drug combination and single drugs are shown in Table 1.

TABLE 1

| Compound | Dose (mg/kg) | PK parameter | Single drug | Triple-drug combination | Increasing rate (%) |
|---|---|---|---|---|---|
| Clomipramine | 2.70 | AUC (ng · h/ml) | 12.7 | 36.3 | 185.8 |
|  |  | $C_{max}$ (ng/ml) | 6.7 | 13.8 | 106.0 |
| Sertraline | 6.02 | AUC (ng · h/ml) | 476.2 | 803.6 | 68.8 |
|  |  | $C_{max}$ (ng/ml) | 81.1 | 95.8 | 18.1 |
| Fluoxetine | 2.41 | AUC (ng · h/ml) | 55.5 | 289.3 | 421.3 |
|  |  | $C_{max}$ (ng/ml) | 23.3 | 62.1 | 166.5 |

As shown in Table 1, the triple-drug combination (clomipramine 2.70 mg/kg, sertraline 6.02 mg/kg and fluoxetine 2.41 mg/kg) led to the increases in AUC and $C_{max}$ when compared with those of the single drug administration. These results demonstrate that AUC and $C_{max}$ were escalated by drug-drug interaction of the triple-drug combination. As a result, the effective ejaculation delay can be expected even with low dose.

Example 2

Pharmacological Effect Evaluation (Rats)

2-1> Materials and Methods

According to the method of *Brain Res Brain Res Protoc*, 1997, (1):203-9, this experiment was executed by employing male and female Crl:CD (SD) rats above 20 weeks old as test animals.

(1) Ovariectomy and Induction of Estrus

The female rats were anesthetized by the intraperitoneal injection of combination of ketamine 75 mg/kg and xylazine 25 mg/kg. After performing laparotomy, the ovaries were removed and peritoneal wall was closed with sutures. 2 ml of 10% ampicillin was injected intraperitoneally and the female rats had recovery period of 7 days. Ovariectomied females were brought into artificial estrus by subcutaneous injection of 20 μg/rat of estradiol benzoate, dissolved in 0.2 ml of sesame oil, about 52 hours before the administration of a test compound, followed by s.c injection of 1 mg/rat of progesterone, dissolved in 0.2 ml of sesame oil, about 4 hours before the administration of a test compound.

(2) Screening Test and Copulatory Experience

Screening test was performed in an observation cage (60× 40×30 cm) with plexiglass front. Before screening test, the male rats were allowed to adapt to the observation cage for 10 minutes and then the female rats with artificial estrus were brought into the cage. If male rats had ejaculated within 30 minutes, they were regarded as sexually active ones. Selected male rats went through copulatory experience for 5 times at 3 days intervals.

(3) Administration and Evaluation

The experienced males were divided into 15 groups of about 10 animals so that the mean ejaculation latency time (ELT) of groups are similar. Test compound was single orally administered.

Group 1 as a negative control was administered with 0.5% methylcellulose 1500 (Sigma Co., hereinafter as "MC 1500"). Groups 2~4 as single drug-administered groups were administered with clomipramine, sertraline and fluoxetine, respectively. Groups 5~7 were administered with double-drug combinations. Groups 8~15 were administered with triple-drug combinations having various doses. Detailed doses are represented in Table 2 below.

After 2 hours and 50 minutes from the administration of test compounds, the male rats were allowed to adapt to the observation cage for 10 minutes. Then copulatory behavior test was initiated with the introduction of female rats with artificial estrus into the observation cage. The ejaculation latency time (ELT) as the time from the first intromission until the ejaculation was evaluated.

<2-2> Results

Figure 1:
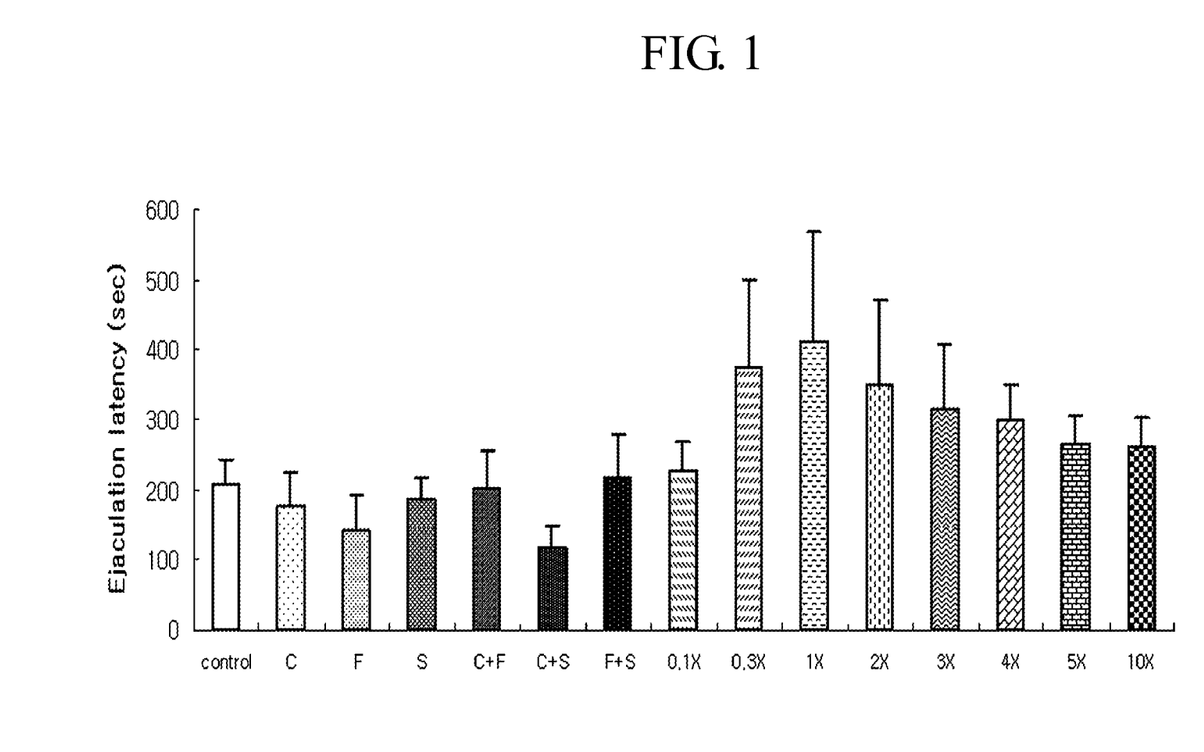
FIG. 1: Change of ejaculation latency time according to Example 2.

Results of ELT on rats from the experiments described above are represented as the mean±S.E.M and are shown in Table 2 and FIG. 1.

TABLE 2

| Group | Test comp. & dose (mg/kg) | Ejaculation latency time, mean ± S.E.M. (sec) | Increasing rate (%) |
|---|---|---|---|
| 1 Negative control | 0.5% MC 1500 | 206.8 ± 37.4 |  |
| 2 Single drug | C: 2.70 | 177.2 ± 47.6 | −14.3 |
| 3 Single drug | S: 6.02 | 185.8 ± 31.7 | −10.2 |
| 4 Single drug | F: 2.41 | 141.3 ± 51.2 | −31.7 |
| 5 Double-drug combination | C: 2.70 + F: 2.41 | 201.3 ± 54.8 | −2.7 |
| 6 Double-drug combination | C: 2.70 + S: 6.02 | 116.1 ± 32.5 | −43.9 |
| 7 Double-drug combination | F: 2.41 + S: 6.02 | 219.4 ± 59.2 | 6.1 |
| 8 Triple-drug combination (0.1X) | C: 0.09 + S: 0.14 + F: 0.07 | 227.0 ± 40.1 | 9.8 |
| 9 Triple-drug combination (0.3X) | C: 0.27 + S: 0.41 + F: 0.21 | 375.5 ± 122.4 | 81.6 |
| 10 Triple-drug combination (1X) | C: 0.90 + S: 1.36 + F: 0.71 | 409.1 ± 158.2 | 97.8 |
| 11 Triple-drug combination (2X) | C: 1.80 + S: 2.72 + F: 1.42 | 350.1 ± 120.3 | 69.3 |

TABLE 2-continued

| Group | Test comp. & dose (mg/kg) | Ejaculation latency time, mean ± S.E.M. (sec) | Increasing rate (%) |
|---|---|---|---|
| 12 Triple-drug combination (3X) | C: 2.70 + S: 4.08 + F: 2.13 | 314.3 ± 92.1 | 52.0 |
| 13 Triple-drug combination (4X) | C: 3.60 + S: 5.44 + F: 2.84 | 300.1 ± 50.3 | 45.1 |
| 14 Triple-drug combination (5X) | C: 4.50 + S: 6.80 + F: 3.55 | 263.7 ± 42.2 | 27.5 |
| 15 Triple-drug combination (10X) | C: 9.00 + S: 13.60 + F: 7.10 | 260.8 ± 43.8 | 26.1 |

(C: clomipramine, S: sertraline, F: fluoxetine)

The ELT of Group 1 (negative control group) was 206.8±37.4 sec. In case of Groups 2~4 (single-drug groups), the ELT was not longer than that of the negative control group. Also, there was no increase of the ELT in Groups 5 and 6 (double-drug combination groups) compared with negative control group.

However, the ELTs of triple-drug combinations (clomipramine+sertraline+fluoxetine) of Group 8 to Group 15 were 227.0±40.1 sec, 375.5±122.4 sec, 409.1±158.2 sec, 350.1±120.3 sec, 314.3±92.1 sec, 300.1±50.3 sec, 263.7±42.2 sec and 260.8±43.8 sec, respectively. The increasing rate (%) of their ELTs compared with the negative control group were 9.8%, 81.6%, 97.8%, 69.3%, 52.0%, 45.1%, 27.5% and 26.1%, respectively.

Considering all the results of the above, all of the triple-drug combinations of Group 8 to Group 15 increased the ELT compared with the negative control group in the dosage of 0.1×~10×. Especially, Group 10 (the triple-drug combination of 1× dose) showed outstanding increasing rate (about 98%) of ELT compared with the negative control group. Also, all the groups of triple-drug combinations were found having excellent effects on delay of ejaculation, compared with the single drugs and the double-drug combinations.

In conclusion, triple-drug combinations (clomipramine, sertraline and fluoxetine) have excellent effects for treating premature ejaculation compared with the single drugs and double-drug combinations.

Example 3

Side Effect Evaluation (Rats)

3-1> Materials and Methods 7-week-old male Crl:CD (SD) rats were divided into five groups of 10 rats. A negative control group was administered with 0.5% MC 1500, and triple-drug combination (clomipramine+fluoxetine+sertraline) group, with 4 doses (indicated with 3×, 5×, 7× and 10×) of the triple-drug combination once a day for 7 days. Detailed doses are represented in Table 3 below. Then animals were observed twice a day for clinical signs, and their body weights were measured before the initiation of the experiment and on the $1^{st}$, $3^{rd}$, $5^{th}$ and $7^{th}$ day from the initiation.

<3-2> Evaluation Methods

Toxic effects of triple-drug combination were evaluated by comparing the treated groups with the negative control group. Especially when the gain or loss of body weights during the experiment period is statistically significant, it is considered as toxic effects.

Statistical analyses for body weight were performed for comparisons between the treated groups and the negative control group. Differences were considered significant for findings of $p<0.05$, $p<0.01$ and $p<0.001$. First, a given parameter was examined by Levene's test for evaluation of homogeneity of variance. If the variance was homogeneous, Dunnett's t-test was used to compare each dose group with the negative control group. If the variance of Levene's test was not homogeneous, the rank-transform test was used to compare each dose group with the negative control group. The transformed data were reexamined by Levene's test for evaluation of homogeneity of variance. If the variance was homogeneous, Dunnett's t-test was used to compare each dose group with the negative control group.

<3-3> Results

Figure 2:
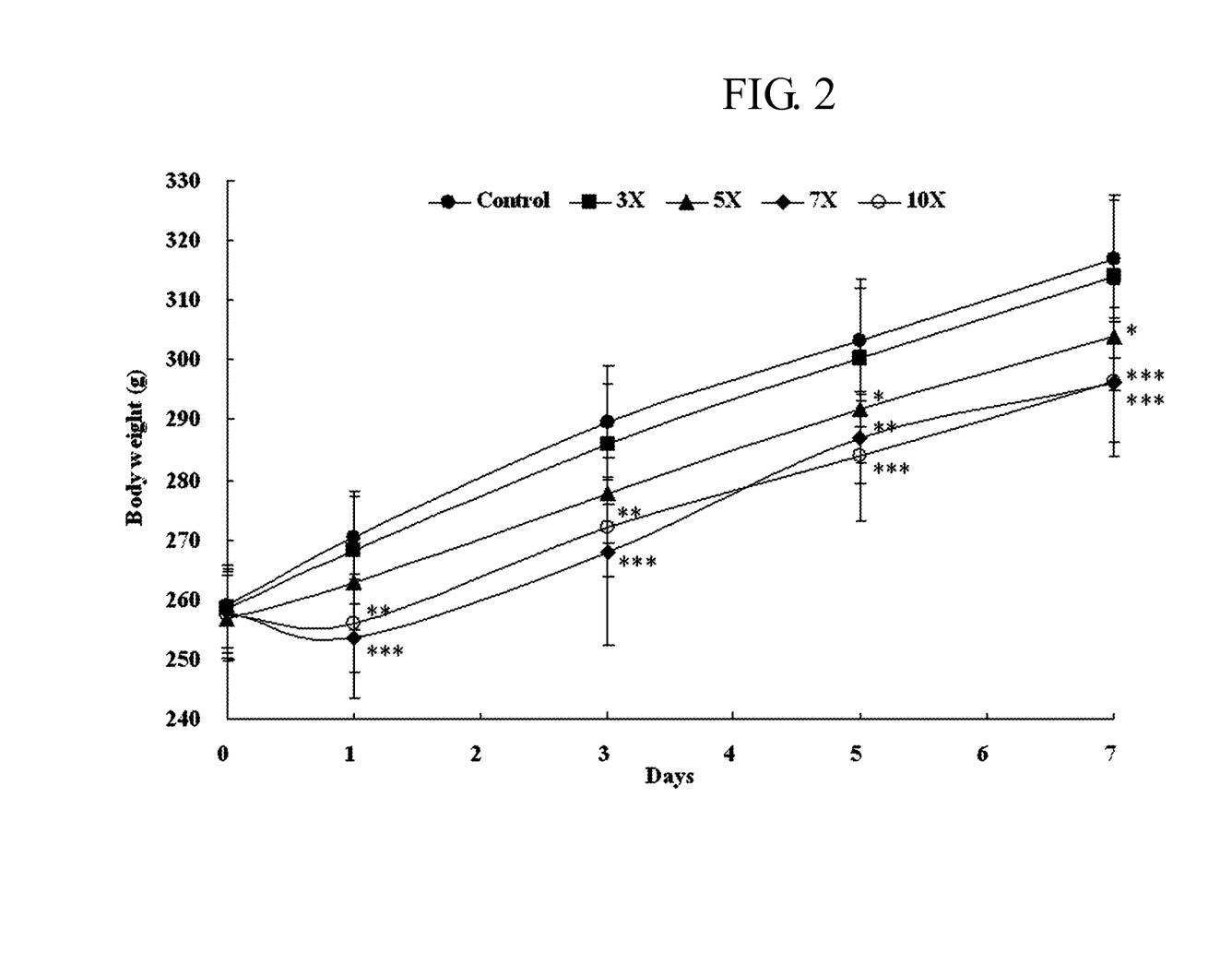
FIG. 2: Change of body weights according to Example 3.

Body weight changes of rats from the experiments described above are represented as the mean±S.D. and are shown in Table 3 and FIG. 2.

TABLE 3

| Dosage (mg/kg/day) | Day | | | | | Body weight change (g) |
|---|---|---|---|---|---|---|
| | 0 | 1 | 3 | 5 | 7 | |
| Negative control (0.5% MC 1500) | 258.89 ± 6.87 | 270.38 ± 7.71 | 289.61 ± 9.40 | 303.33 ± 10.05 | 316.82 ± 9.74 | 57.9 |
| 3X (C: 2.70 + S: 4.08 + F: 2.13) | 258.43 ± 7.36 | 268.25 ± 9.08 | 286.01 ± 10.05 | 300.43 ± 11.48 | 313.94 ± 13.52 | 55.5 |
| 5X (C: 4.50 + S: 6.80 + F: 3.55) | 256.90 ± 7.26 | 262.93 ± 7.80 | 277.82 ± 8.41 | * 291.85 ± 9.04 | * 303.88 ± 8.82 | 47.0 |

TABLE 3-continued

| Dosage (mg/kg/day) | 0 | 1 | 3 | 5 | 7 | Body weight change (g) |
|---|---|---|---|---|---|---|
| 7X (C: 6.30 + S: 9.52 + F: 4.97) | 258.11 ± 6.94 | *** 253.57 ± 9.82 | *** 268.08 ± 15.58 | *** 286.89 ± 7.38 | *** 296.27 ± 10.15 | 38.2 |
| 10X (C: 9.00 + S: 13.60 + F: 7.10) | 257.57 ± 7.29 | ** 256.10 ± 8.33 | ** 272.16 ± 8.33 | *** 283.92 ± 10.88 | *** 296.42 ± 12.36 | 38.9 |

(C: clomipramine, S: sertraline, F: fluoxetine)
Each values of the experiment were represented as the mean (weight, (g)) ± S.D.
*, , *: Significantly different from the negative control at p < 0.05, p < 0.01 and p < 0.001, respectively.

Body weight change compared with a negative control group has been used as a representative factor to evaluate the toxicological sign of a drug. When the triple-drug combination was administered for 7 days, the body weight decreased about 4% on days 5 and 7 in the 5× Group compared with the negative control group. Further, body weights significantly decreased about 6~8% on days 1 to 7 in the 7× and 10× Group compared with the negative control group. When the body weight change for 7 days of each treatment groups was compared with the negative control group, the body weight gain significantly decreased by −19%, −34% and −33% for 5×, 7×, and 10× groups, respectively. The maximum tolerated dose (MTD) is generally chosen based on decrease of less than 10% in body weight gain compared with a negative control in the toxicity study. According to the above results, the MTD of triple-drug combinations in the present invention was determined as below 5× dose.

Example 4

Pharmacological Effect Evaluation—Clinical Study

<4-1> Calculation of Human Dose

Based on the rat dose of Example 2, the human dose can be calculated. More specifically, based on US FDA's guide, "Estimating the Maximum Safe Starting Dose in Initial Clinical Trials for Therapeutics in Adult Healthy Volunteers", the human equivalent dose (HED) can be calculated by using the calculating formula below. The calculation is based on the assumption that a rat is 150 g, and a person is 60 kg.

HED=animal dose(mg/kg)×(animal weight(kg)/human weight(kg))$^{0.33}$

As to the triple-drug combination of the present invention, if 1× dose of a rat is converted into the human body dose, it is calculated as clomipramine 7.4 mg, sertraline 11.2 mg, and fluoxetine 6.0 mg. Based on Example 2, the rat doses of Groups 8~15 are converted into the human body doses as to the triple-drug combination. Detailed human body doses are represented in Table 4 below.

TABLE 4

| Group | Test comp. & dose (mg) | | |
|---|---|---|---|
| | Clomipramine | Sertraline | Fluoxetine |
| 0.1X | 0.7 | 1.1 | 0.5 |
| 0.3X | 2.2 | 3.3 | 1.7 |
| 1X | 7.5 | 11.3 | 5.9 |
| 2X | 15.0 | 22.6 | 11.8 |
| 3X | 22.5 | 33.9 | 17.7 |
| 4X | 30.0 | 45.2 | 23.6 |
| 5X | 37.5 | 56.5 | 29.5 |
| 7X | 52.5 | 79.1 | 41.3 |
| 10X | 75.0 | 113.0 | 59.0 |

<4-2> Experimental Method

Patients with premature ejaculation of 60 seconds or less were divided into 4 groups of twenty people. The patient group 1 was administered as a daily dose with clomipramine 22.4 mg; the patient group 2, with sertraline 50.0 mg; the patient group 3, with fluoxetine 20.0 mg; and the patient group 4, with the triple-drug combination of the present invention including clomipramine 7.5 mg, sertraline 11.3 mg, and fluoxetine 5.9 mg. A dose was taken 3 hours before the sexual intercourse begins, and the administration period was for 3 weeks. The effect of the administration of the drugs to the patients examined through interviews with the patients. A drug was determined as effective when the patient's ejaculation latency time had been 10 minutes or more.

<4-3> Results

Results of the human treatment effect from the experiments described above are shown in Table 5.

TABLE 5

| Patient group and dose | No. of Patients | Patient no. with ELT of 10 min or over | Treatment effect (%) |
|---|---|---|---|
| Clomipramine (22.4 mg) | 20 | 15 | 75 |
| Sertraline (50.0 mg) | 20 | 8 | 40 |
| Fluoxetine (20.0 mg) | 20 | 0 | — |
| Inventive triple-drug combination (C: 7.5 mg + S: 11.3 mg + F: 5.9 mg) | 20 | 19 | 95 |

(C: clomipramine, S: sertraline, F: fluoxetine)

As shown in Table 5, curative effects of the drugs were exhibited in 75% of the patients administered with clomipramine 22.4 mg and about 40% of patients administered with sertraline 50.0 mg. However, the curative effect did not show up in the patients administered with fluoxetine 20.0 mg. In stark contrast, in the case of patients administered with the triple-drug combination, curative effect appeared in surprising 95% of them, despite of the significantly reduced doses of each drugs.

Example 5

Side Effect Evaluation—Clinical Study (Nausea)

A side effect incidence rate of nausea was investigated among patients who took each drug in Example 4. As shown in Table 6, the nausea occurred in 90% of the patients who took sertraline 50.0 mg, while only 5% of the patients who took the triple-drug combination experienced the nausea. This result demonstrates the notable nausea diminishing effect of the triple-drug combination.

Results of the side effect (nausea) from the experiments described above are shown in Table 6.

TABLE 6

| Patient group and dose | No. of Patients | No. of nausea | Incidence rate (%) |
|---|---|---|---|
| Sertraline (50.0 mg) | 20 | 18 | 90 |
| Inventive triple-drug combination (C: 7.5 mg + S: 11.3 mg + F: 5.9 mg) | 20 | 1 | 5 |

(C: clomipramine, S: sertraline, F: fluoxetine)

Example 6

Side Effect Evaluation—Clinical Study (Sedation)

A side effect incidence rate of sedation was investigated among patients who took each drug in Example 4. As shown in Table 7, the sedation occurred in 70% of the patients who took clomipramine 22.4 mg, while about 5% of the patients who took the triple-drug combination experienced the sedation. This result demonstrates the notable sedation diminishing effect of the triple-drug combination.

Results of the side effect from the experiments described above are shown in Table 7.

TABLE 7

| Patient group and dose | No. of Patients | No. of sedation | Incidence rate (%) |
|---|---|---|---|
| Clomipramine (22.4 mg) | 20 | 14 | 70 |
| Inventive triple-drug combination (C: 7.5 mg + S: 11.3 mg + F: 5.9 mg) | 20 | 1 | 5 |

(C: clomipramine, S: sertraline, F: fluoxetine)

Formulation Example 1

Preparation of Tablet

All ingredients of the tablet core shown in Table 8, including clomipramine hydrochloride, sertraline hydrochloride and fluoxetine hydrochloride as active ingredients, were mixed thoroughly and then compressed using a single tablet press to obtain tablets. The tablets were coated with Opadry® (the Opadry white 85F 18422, the Colorcon Corp) to obtain film-coated tablets.

TABLE 8

| | Component | mg/tablet |
|---|---|---|
| Tablet core | Clomipramine hydrochloride | 8.4 |
| | (Clomipramine free base) | (7.5) |
| | Sertraline hydrochloride | 12.6 |
| | (Sertraline free base) | (11.3) |
| | Fluoxetine hydrochloride | 6.6 |
| | (Fluoxetine free base) | (5.9) |
| | Microcrystalline cellulose | 116.4 |
| | D-mannitol | 40.0 |
| | Hydroxypropyl cellulose | 6.0 |
| | Croscarmellose sodium | 6.0 |
| | Sodium lauryl sulfate | 2.0 |
| | Magnesium stearate | 2.0 |

TABLE 8-continued

| | Component | mg/tablet |
|---|---|---|
| Coating layer | Opadry ® | 6.0 |
| Total weight | | 206.0 |

Formulation Example 2

Preparation of Tablet

All ingredients of the granule inside shown in Table 9, including clomipramine hydrochloride, sertraline hydrochloride and fluoxetine hydrochloride as active ingredients, were mixed. A binder solution prepared by dissolving hydroxypropyl cellulose and polysorbate 80 in water was added thereto to obtain granules. Magnesium stearate was added to the granules and the mixture was compressed to obtain tablets. The tablets were coated with Opadry® to obtain film-coated tablets.

TABLE 9

| | | Component | mg/tablet |
|---|---|---|---|
| Tablet core | Granule Inside | Clomipramine hydrochloride | 8.4 |
| | | (Clomipramine free base) | (7.5) |
| | | Sertraline hydrochloride | 12.6 |
| | | (Sertraline free base) | (11.3) |
| | | Fluoxetine hydrochloride | 6.6 |
| | | (Fluoxetine free base) | (5.9) |
| | | Microcrystalline cellulose | 112.8 |
| | | Sodium starch glycolate | 8.0 |
| | Binder solution | Hydroxypropyl cellulose | 6.0 |
| | | Polysorbate 80 | 4.0 |
| | Granule outside | Magnesium stearate | 1.6 |
| Coating layer | | Opadry ® | 5.0 |
| Total weight | | | 165.0 |

Formulation Example 3

Preparation of Capsule

All ingredients shown in Table 10, including clomipramine hydrochloride, sertraline hydrochloride and fluoxetine hydrochloride as active ingredients were mixed thoroughly. The resulting mixture was filled in hard (gelatin) to give capsules.

TABLE 10

| Component | mg/capsule |
|---|---|
| Clomipramine hydrochloride | 8.4 |
| (Clomipramine free base) | (7.5) |
| Sertraline hydrochloride | 12.6 |
| (Sertraline free base) | (11.3) |
| Fluoxetine hydrochloride | 6.6 |
| (Fluoxetine free base) | (5.9) |
| Microcrystalline cellulose | 113.4 |
| Corn starch | 50.0 |
| Sodium starch glycolate | 5.0 |
| Sodium lauryl sulfate | 2.0 |
| Magnesium stearate | 2.0 |
| Total weight | 200.0 |

While the invention has been described with respect to the above specific embodiments, it should be recognized that various modifications and changes may be made to the invention by those skilled in the art which also fall within the scope of the invention as defined by the appended claims.

What is claimed is:

1. A pharmaceutical composition consisting essentially of clomipramine or a pharmaceutically acceptable salt thereof, sertraline or a pharmaceutically acceptable salt thereof and fluoxetine or a pharmaceutically acceptable salt thereof as active ingredients, wherein clomipramine or a pharmaceutically acceptable salt thereof, sertraline or a pharmaceutically acceptable salt thereof and fluoxetine or a pharmaceutically acceptable salt thereof are contained in a weight ratio of 1:1~2:0.5~1.

2. The composition of claim 1, wherein the pharmaceutically acceptable salt is a hydrochloride.

3. The composition of claim 1, which further comprises a pharmaceutically acceptable carrier.

4. The composition of claim 3, wherein the pharmaceutically acceptable carrier is selected from the group consisting of excipients, disintegrants, binders, lubricants, emulsifiers, suspending agents, stabilizers, sweeteners, flavoring agents and a combination thereof.

5. The composition of claim 1, which further comprises a drug selected from the group consisting of serotonin agonists, serotonin antagonists, adrenergic agonists, adrenergic antagonists, adrenergic neuron blockers, impotence treatment drugs, phosphodiesterase 5 inhibitors, erection inducers and a combination thereof.

6. An oral unit dosage form comprising the composition of claim 1 and a pharmaceutically acceptable carrier.

7. The oral unit dosage form of claim 6, which is selected from the group consisting of tablet, capsule, suspension, granule, gel, pill, tincture, decoction, infusion, spirit, fluid extract, elixir, extract, syrup, powder, aromatic water and lemonade.

8. The oral unit dosage form of claim 6, which comprises 0.7~75.0 mg of clomipramine, 1.1~113.0 mg of sertraline and 0.5~59.0 mg of fluoxetine.

9. The oral unit dosage form of claim 6, which comprises 0.7~22.5 mg of clomipramine, 1.1~33.9 mg of sertraline and 0.5~17.7 mg of fluoxetine.

10. The oral unit dosage form of claim 6, which comprises 2.2~22.5 mg of clomipramine, 3.3~33.9 mg of sertraline and 1.7~17.7 mg of fluoxetine.

11. The oral unit dosage form of claim 6, wherein the pharmaceutically acceptable carrier is selected from the group consisting of excipients, disintegrants, binders, lubricants, emulsifiers, suspending agents, stabilizers, sweeteners, flavoring agents and a combination thereof.

12. The oral unit dosage form of claim 6, which further comprises a drug selected from the group consisting of serotonin agonists, serotonin antagonists, adrenergic agonists, adrenergic antagonists, adrenergic neuron blockers, impotence treatment drugs, phosphodiesterase 5 inhibitors, erection inducers and a combination thereof.

* * * * *